US00PP17897P2

(12) United States Plant Patent
Fick

(10) Patent No.: US PP17,897 P2
(45) Date of Patent: Aug. 7, 2007

(54) *SUTERA* PLANT NAMED 'BUSHY WHITE'

(50) Latin Name: *Sutera hybrida*
Varietal Denomination: Bushy White

(76) Inventor: Paul Fick, P.O. Box 4183, George East, 6539 (ZA)

( * ) Notice: Subject to any disclaimer, the term of this patent is extended or adjusted under 35 U.S.C. 154(b) by 0 days.

(21) Appl. No.: 11/349,690

(22) Filed: Feb. 7, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Sutera* plant named 'Bushy White', characterized by its outwardly spreading and low mounding plant habit; vigorous growth habit; freely branching habit; and numerous large white-colored flowers.

1 Drawing Sheet

Botanical designation: *Sutera hybrida.*
Cultivar denomination: 'Bushy White'.

BACKGROUND OF THE INVENTION

The present Invention relates to a new and distinct cultivar of *Sutera* plant, botanically known as *Sutera hybrida,* and hereinafter referred to by the cultivar name 'Bushy White'.

The new *Sutera* originated from a cross-pollination in May, 2001 of an unnamed selection of *Sutera hispida,* not patented, as the female, or seed, parent with an unnamed selection of *Sutera hybrida,* not patented, as the male, or pollen, parent. The cultivar Bushy White was discovered and selected by the Inventor as a flowering plant within the progeny from the aforementioned cross-pollination in a controlled environment in George, South Africa in July, 2001.

Asexual reproduction of the new cultivar by terminal cuttings in George, South Africa since November, 2001, has shown that the unique features of this new *Sutera* are stable and reproduced true to type in successive generations.

SUMMARY OF THE INVENTION

Plants of the cultivar Bushy White have not been observed under all possible environmental conditions. The phenotype may vary somewhat with variations in environment such as temperature and light intensity without, however, any variance in genotype.

The following traits have been repeatedly observed and are determined to be the unique characteristics of 'Bushy White'. These characteristics in combination distinguish 'Bushy White' as a new and distinct cultivar of *Sutera:*

1. Outwardly spreading and low mounding plant habit.
2. Vigorous growth habit.
3. Freely branching habit.
4. Numerous large white-colored flowers.

Compared to plants of the female parent selection, plants of the new *Sutera* have longer and narrower leaves and larger flowers.

Compared to plants of the male parent selection, plants of the new *Sutera* have larger leaves and larger flowers. In addition, plants of the new *Sutera* and the male parent selection differ in leaf and flower color as plants of the male parent selection have lighter green-colored leaves and mauve to white-colored flowers.

Plants of the new *Sutera* can be compared to plants of the *Sutera hispida* cultivar Giant Cloud, not patented. In side-by-side comparisons, plants of the new *Sutera* differed from plants of the cultivar Giant Cloud in the following characteristics:

1. Plants of the new *Sutera* were not as flat and spreading as plants of the cultivar Giant Cloud.
2. Plants of the new *Sutera* were faster growing than plants of the cultivar Giant Cloud.
3. Plants of the new *Sutera* had larger leaves and flowers than plants of the cultivar Giant Cloud.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Sutera.*

The photograph at the bottom of the sheet comprises a side perspective view of a typical flowering plant of 'Bushy White' grown in a container.

The photograph at the top of the sheet comprises a close-up view of typical flowers and leaves of 'Bushy White'.

DETAILED BOTANICAL DESCRIPTION

The aforementioned photographs and following observations and measurements describe plants grown in Bonsall, Calif., in an outdoor nursery during the summer with day temperatures ranging from 18° C. to 35° C. and night temperatures ranging from 13° C. to 18° C. Plants were grown in 15-cm containers and were about three months old.

Color references are made to The Royal Horticultural Society Colour Chart, 1995 Edition, except where general terms of ordinary dictionary significance are used.

Botanical classification: *Sutera hybrida* cultivar Bushy White.

Parentage:

*Female, or seed, parent.*—An unnamed selection of *Sutera hispida,* not patented.

*Male, or pollen, parent.*—An unnamed selection of *Sutera hybrida,* not patented.

Propagation:

*Type cutting.*—Terminal vegetative cuttings.

*Time to initiate roots.*—About 15 days.

*Time to produce a rooted young plant.*—About three to four weeks.

*Root description.*—Fine, fibrous; white in color.

*Rooting habit.*—Freely branching; dense.

Plant description:

*Form.*—Outwardly spreading and low mounding plant habit. Freely and continuously branching with about six primary lateral branches each with about eight secondary lateral branches. Vigorous growth habit.

*Plant height.*—About 12 cm.

*Plant diameter.*—About 62 cm.

*Lateral branches.*—Length: About 47 cm. Diameter: About 4 mm. Internode length: About 2 cm. Texture: Pubescent; minute. Strength: Strong. Color, young stems: 144A. Color, mature stems: 199A to 199B.

*Foliage description.*—Arrangement: Opposite; simple. Length: About 3 cm. Width: About 1.6 cm. Shape: Elliptic. Apex: Broadly acute. Base: Attenuate. Margin: Nearly entire with shallow irregular serrations. Texture, upper and lower surfaces: Pubescent; minute. Venation pattern: Pinnate, arcuate. Color: Developing foliage, upper surface: 146A. Developing foliage, lower surface: 146B. Fully expanded foliage, upper surface: 147A; venation, 147B. Fully expanded foliage, lower surface: 147B; venation, 147B. Petiole length: About 4 mm. Petiole diameter: About 2 mm. Petiole texture, upper and lower surfaces: Sparsely pubescent. Petiole color, upper and lower surfaces: 147B.

Flower description:

*Flower type and habit.*—Solitary axillary flowers; salverform; slender corolla tubes flare abruptly into five rounded lobes. Flowers persistent. Very freely flowering; typically about 31 to 32 flower buds and open flowers per lateral branch. Flowers face mostly upward or outward. Flowers persistent.

*Natural flowering season.*—Plants typically flower from spring until fall; flowering continuous during this period.

*Flower longevity on the plant.*—About seven days.

*Fragrance.*—None detected.

*Flower diameter.*—About 1.5 cm.

*Flower depth.*—About 1.4 cm.

*Flower buds.*—Length: About 1 cm. Diameter: About 4 mm. Shape: Obovate. Color: 157A.

*Corolla.*—Quantity/arrangement: Five fused petals; slender corolla tube flaring abruptly into five rounded lobes. Petal lobe length from throat: About 7 mm. Petal lobe width: About 5 mm. Petal lobe shape: Roughly spatulate. Petal lobe apex: Rounded. Petal lobe margin: Entire. Texture, upper and lower surfaces: Smooth, glabrous. Color: When opening, upper and lower surfaces: Close to 155D. Fully opened, upper and lower surfaces: Close to 155D. Flower throat (inside): 23A. Flower tube (outside): Close to 155D.

*Sepals.*—Arrangement/appearance: Single whorl of five sepals fused at base; star-shaped calyx. Length: About 6 mm. Width: About 1 mm. Shape: Narrow, linear. Apex: Acute. Margin: Entire. Texture, upper and lower surfaces: Slightly rough. Color, upper and lower surfaces: 143A.

*Peduncles.*—Length: About 1 cm. Width: About 1 mm. Angle: About 30° to 45° from the stem. Strength: Moderately strong to strong. Texture: Pubescent; minute. Color: 145C.

*Reproductive organs.*—Stamens: Quantity per flower: Four. Anther shape: Oval. Anther length: Less than 1 mm. Anther color: 14A. Pollen amount: Scarce. Pollen color: 23A. Pistils: Quantity per flower: One. Pistil length: About 1.2 cm. Style length: About 1 cm. Style color: 145D. Stigma shape: Round. Stigma color: 145A. Ovary color: 145A.

*Seed/fruit.*—Seed and fruit production has not been observed.

Disease/pest resistance: Plants of the new *Sutera* have not been noted to be resistant to pathogens or pests common to *Sutera.*

Garden performance: Plants of the new *Sutera* have been observed to have good garden performance. Plants of the new *Sutera* tolerate temperatures from about 2° C. to 38° C. and to tolerate wind and rain.

It is claimed:

1. A new and distinct cultivar of *Sutera* plant named 'Bushy White', as illustrated and described.

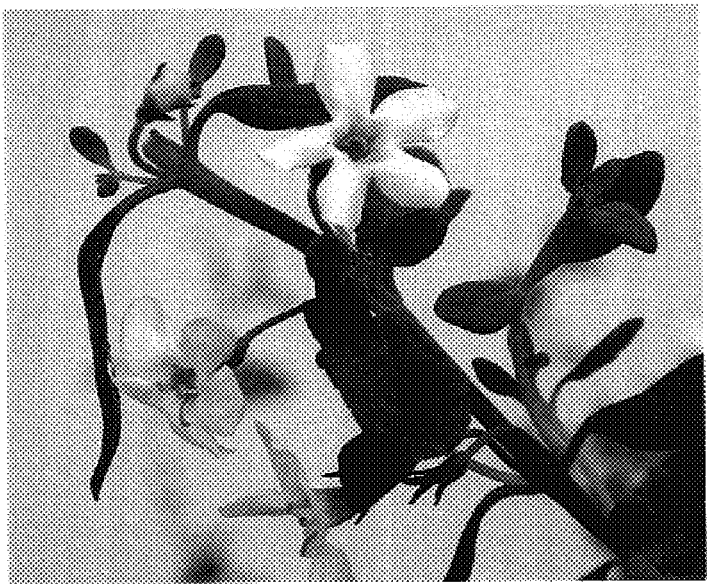
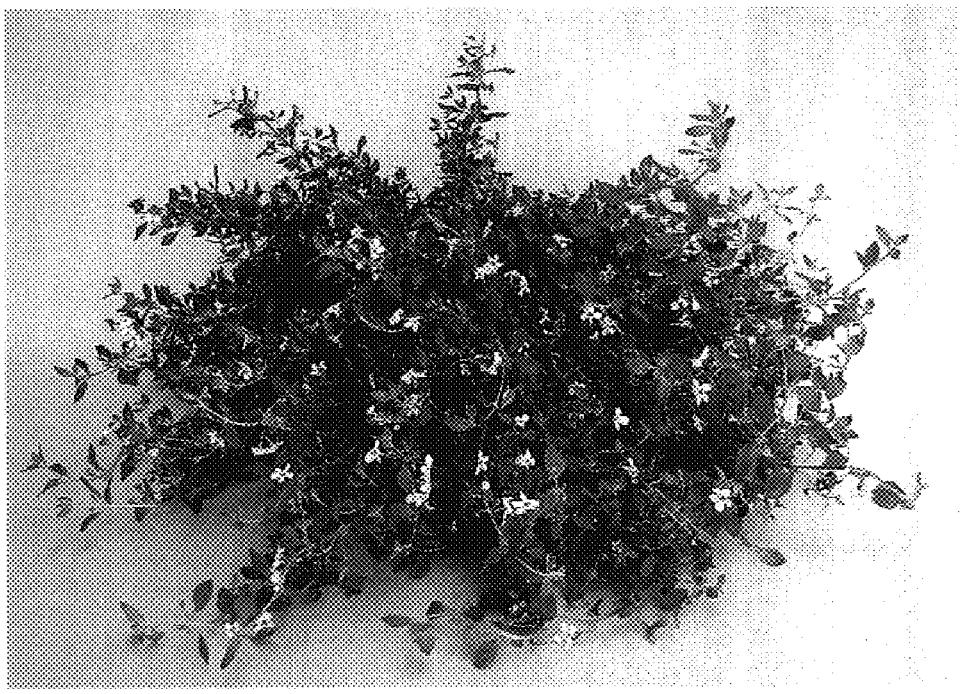

* * * * *